(12) United States Patent
Stenzler et al.

(10) Patent No.: US 8,932,261 B2
(45) Date of Patent: Jan. 13, 2015

(54) VALVE ASSEMBLY FOR RESPIRATORY SYSTEMS

(75) Inventors: Alex Stenzler, Long Beach, CA (US); Steve Han, Upland, CA (US)

(73) Assignee: Carefusion 207, Inc., San Diego, CA (US)

(*) Notice: Subject to any disclaimer, the term of this patent is extended or adjusted under 35 U.S.C. 154(b) by 1041 days.

(21) Appl. No.: 12/511,395

(22) Filed: Jul. 29, 2009

(65) Prior Publication Data

US 2010/0024823 A1    Feb. 4, 2010

Related U.S. Application Data

(60) Provisional application No. 61/084,424, filed on Jul. 29, 2008.

(51) Int. Cl.
| | |
|---|---|
| *A61M 39/00* | (2006.01) |
| *A61M 16/20* | (2006.01) |
| *A61M 16/00* | (2006.01) |
| *A62B 9/02* | (2006.01) |
| *A61M 16/04* | (2006.01) |

(Continued)

(52) U.S. Cl.
CPC ........ *A61M 16/0463* (2013.01); *A61M 16/0816* (2013.01); *A61M 39/045* (2013.01); *A61M 2039/1077* (2013.01)
USPC ............ 604/167.04; 128/207.14; 128/207.16; 128/205.24; 604/167.01

(58) Field of Classification Search
USPC ............. 128/200.24, 202.27, 200.26, 204.18, 128/203.12, 207.14, 207.15, 207.16, 128/205.24, 205.19; 604/167.01, 167.04; 623/23.68
See application file for complete search history.

(56) References Cited

U.S. PATENT DOCUMENTS

| | | |
|---|---|---|
| 4,558,708 A | 12/1985 | Labuda et al. |
| 4,569,344 A | 2/1986 | Palmer |

(Continued)

FOREIGN PATENT DOCUMENTS

| | | |
|---|---|---|
| DE | 10 2005 014650 B3 | 8/2006 |
| EP | 1911482 A2 | 4/2008 |

(Continued)

OTHER PUBLICATIONS

PCT Search Report (mailed Nov. 2, 2009); 19 pgs.

(Continued)

*Primary Examiner* — Loan H Thanh
*Assistant Examiner* — Sundhara Ganesan
(74) *Attorney, Agent, or Firm* — McDermott Will & Emery LLP

(57) ABSTRACT

An adapter assembly including a manifold and a valve assembly. The valve assembly includes a seat and a valve body having a circular base and a wall. The wall extends from a trailing side of the base to form a dome-like shape terminating at an end at which a slit is formed, with the wall defining opposing sealing edges at the slit. The seat has an upper circumferential surface and a lower circumferential surface. The upper surface engages a leading side of the base, whereas the lower surface engages a trailing side. At least one of the upper and lower surfaces forms a segment of increased height. Upon final assembly, the valve body is disposed across a passageway of the manifold, with the slit providing a selectively openable path. A force imparted by the segment of increased height flexes the base and biases the sealing edges into engagement.

11 Claims, 14 Drawing Sheets

(51) Int. Cl.
  *A61M 16/08* (2006.01)
  *A61M 39/04* (2006.01)
  *A61M 39/10* (2006.01)

(56) References Cited

U.S. PATENT DOCUMENTS

| | | |
|---|---|---|
| 4,723,543 A | 2/1988 | Beran |
| 4,815,459 A | 3/1989 | Beran |
| 5,261,459 A | 11/1993 | Atkinson et al. |
| 5,492,304 A * | 2/1996 | Smith et al. ............... 251/149.1 |
| 5,501,214 A * | 3/1996 | Sabo ....................... 128/205.24 |
| 5,642,726 A | 7/1997 | Owens et al. |
| 5,730,123 A | 3/1998 | Lorenzen et al. |
| 5,735,271 A | 4/1998 | Lorenzen et al. |
| 5,906,595 A * | 5/1999 | Powell et al. ............ 604/167.01 |
| 6,572,590 B1 | 6/2003 | Stevens et al. |
| 6,588,425 B2 | 7/2003 | Rouns et al. |
| 6,609,520 B1 | 8/2003 | Carlsen et al. |
| 6,997,393 B1 | 2/2006 | Angold et al. |
| 7,059,322 B2 | 6/2006 | Rich et al. |
| 7,188,623 B2 | 3/2007 | Anderson et al. |
| 7,191,782 B2 | 3/2007 | Madsen |
| 7,530,369 B2 * | 5/2009 | Anderson ..................... 137/846 |
| 2003/0085373 A1 | 5/2003 | Dehdashtian |
| 2003/0109853 A1 | 6/2003 | Harding et al. |
| 2003/0234015 A1 * | 12/2003 | Bruce et al. .............. 128/200.23 |
| 2005/0113757 A1 * | 5/2005 | McFarlane ................ 604/167.03 |
| 2006/0276751 A1 | 12/2006 | Haberland et al. |

FOREIGN PATENT DOCUMENTS

| | | |
|---|---|---|
| JP | H07-508192 A | 9/1995 |
| JP | 2004535840 A | 12/2004 |
| WO | 2006/076571 A1 | 7/2006 |
| WO | 2006086069 A2 | 8/2006 |
| WO | 2007/105779 A1 | 9/2007 |
| WO | 2007146613 A2 | 12/2007 |

OTHER PUBLICATIONS

New Zealand Examination Report, Appln. No. 591386, dated Feb. 3, 2012 (2 pages).
Office Action for JP Patent Application No. 2011-521295 issued Jul. 9, 2013.
Office Action for RU Patent Application No. 2011107226 issued May 4, 2013.

* cited by examiner

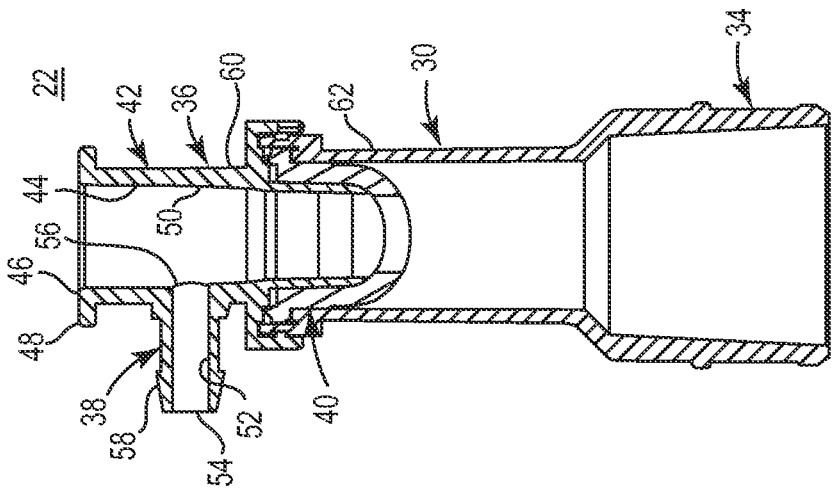
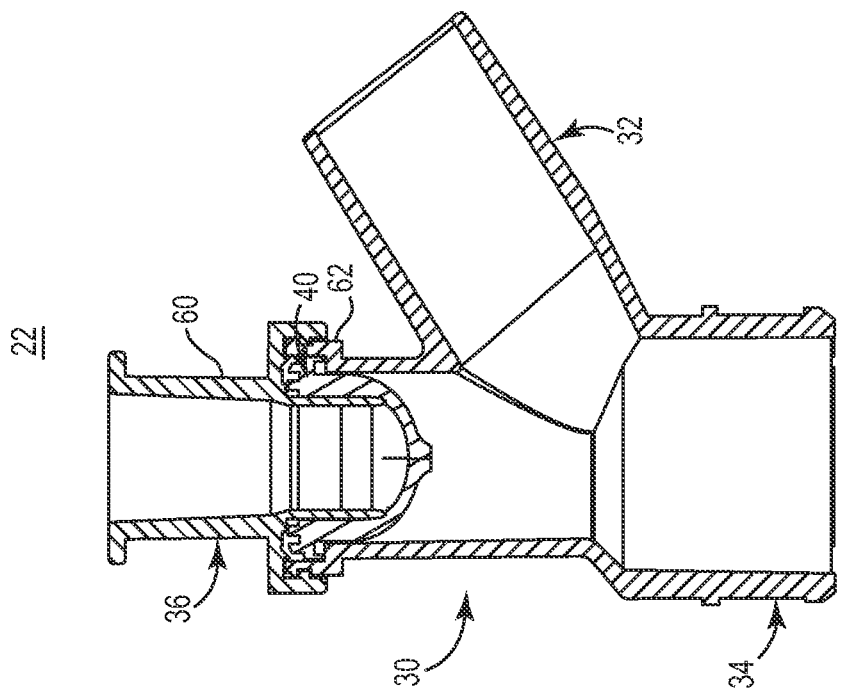

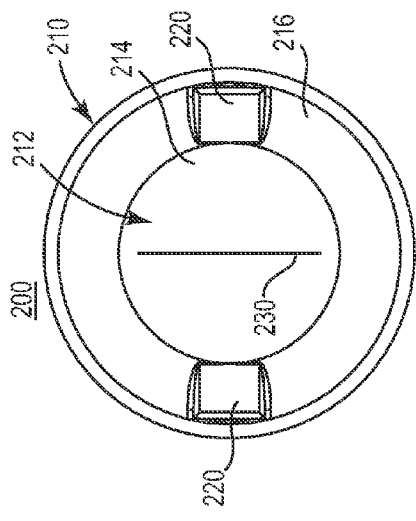
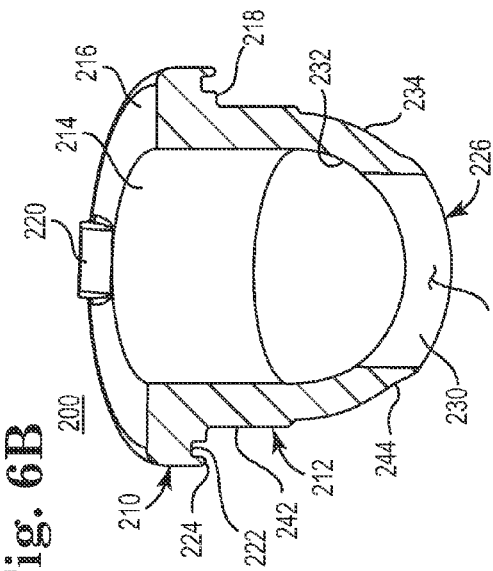
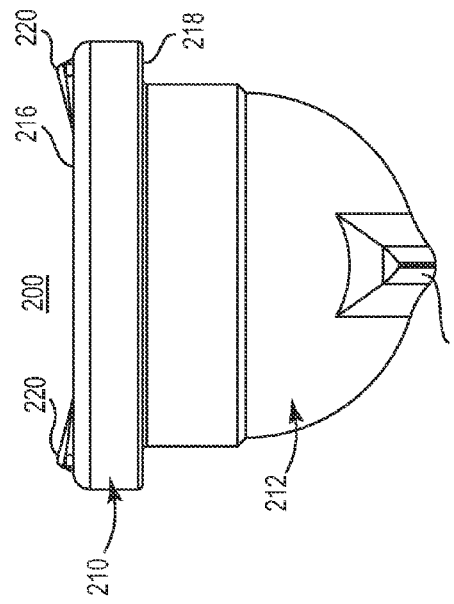
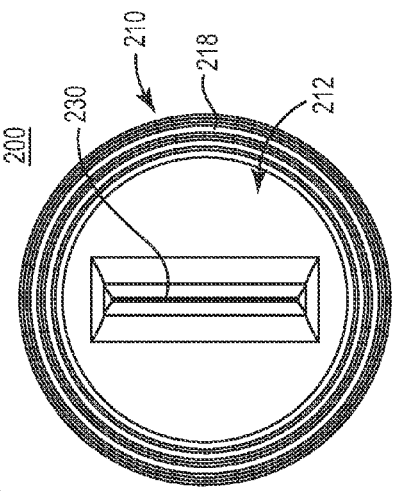

VALVE ASSEMBLY FOR RESPIRATORY SYSTEMS

CROSS-REFERENCE TO RELATED APPLICATION

This application claims priority to U.S. Provisional Patent Application Ser. No. 61/084,424, filed Jul. 29, 2008, the entire teachings of which are incorporated herein by reference.

BACKGROUND

The present disclosure relates generally to airway access adapters used in respiratory applications. More particular, it relates to adapters and related closed suction catheter systems with enhanced cleaning or flushing capabilities, as well as optional valve configurations useful therewith.

Use of ventilators and related breathing circuits to assist in patient breathing is well known in the art. For example, during surgery and other medical procedures, the patient is often connected to a ventilator to provide respiratory gases to the patient. In many instances, the mechanical ventilation is connected into the patient's respiratory tract via an artificial airway, such as a tracheostomy tube, endotracheal tube, etc.

While the breathing circuit can establish a single, direct fluid connection between the ventilator and the artificial airway, in many instances, caregivers desire the ability to introduce instruments and/or materials into the breathing circuit. To satisfy these needs, airway access adapters have been developed. In general terms, an airway access adapter is a manifold-type body providing at least three fluidly connected ports including a ventilator port, a respiratory port, and an access port. During use, the airway access adapter is assembled to the breathing circuit with the ventilator fluidly connected to the ventilator port and the artificial airway fluidly connected to the respiratory port. With this configuration, the access port enables caregivers to, for example, insert instruments for visualization or related procedures, or to aspirate fluid or secretions from the patient's airway. Typically, the airway access adapter provides a seal or valve configuration across the access port so that pressures required to maintain ventilation of the patient are not lost via the access port. Airway access adapters are well accepted, and are highly beneficial especially with patients requiring long-term mechanical ventilation.

As indicated above, the airway access adapter facilitates use of a variety of different tools within the breathing circuit. One such tool is a closed suction catheter system used to remove secretions or fluids from the airways of a ventilated patient. To prevent loss of ventilating pressures, the catheter is made part of the sealed breathing circuit so that the circuit does not need to be "opened" in order to suction the patient's airways. Additionally, so that the catheter can remain uncontaminated by environmental micro-organisms, or contaminated by caregivers, the closed suction catheter system oftentimes includes a sheath that covers the portion of the catheter outside the breathing circuit. With this configuration, the closed suction catheter system can be left attached to the breathing circuit (via the airway access adapter) between suctioning procedures. Over time, however, secretions and other materials may accumulate at the working end of the catheter, necessitating periodic cleaning of the catheter. One common cleaning approach entails flushing the catheter end with a fluid such as saline or water to maintain patency and to prevent a stagnation of a media for bacterial growth.

Existing closed suction catheter systems and related airway access adapters employ one of two configurations that enable flushing of the suction catheter system. With one approach, the suction catheter is readily removed from the airway access adapter, and incorporates a flush port otherwise attached to the suction catheter components that facilitates cleaning. With this approach, the flush port is removed from the airway access adapter along with other components of the suctioning catheter system. Conversely, where the suction catheter system (and related airway access adapter) is solely for closed suction applications (i.e., the catheter cannot be detached from the airway access adapter), a flush port is provided with the airway access adapter itself. Since the catheter cannot be removed, the flush port is located so as to introduce the cleaning fluid near the tip of the catheter when the catheter is fully withdrawn from the patient's airway and into the protective sheath.

While the two suction catheter cleaning configurations described above are highly useful, certain drawbacks remain. With removable catheter/flush port designs, other instruments passed into the access port of the airway access adapter (following the removal of the closed suction catheter system) are not easily cleaned. That is to say, once the flush port is removed, it is no longer available for facilitating cleaning of other instruments. Conversely, with available airway access adapters incorporating a flush port, the suction catheter is not readily removed, and cannot be replaced with other instruments, thus limiting an overall usefulness of the adapter. Along these same lines, modifying an airway access adapter having a flush port to removably accept a suction catheter (via a slip fit seal) would result in the slip fit seal blocking the flush port, and thus is not viable.

In addition to the drawbacks associated with current flush port configurations, airway access adapters commonly include a valve of some type that closes the access port during periods of non-use, and promotes sealed insertion of various instruments therethrough. In this regard, conventional check valves and/or flap valves are widely employed, but long-term, repeated sealing of the valve is less than optimal.

In light of the above, needs exist for improved airway access adapters as well as closed suction catheter systems used therewith.

SUMMARY

One aspect provides an adapter assembly for connecting a respiratory device to an artificial airway of a patient, including a manifold and a valve assembly. The manifold forms and fluidly interconnects a ventilator port, a respiratory port, and an access port. The manifold has a conduit forming a passageway extending from, and fluidly connected to, the access port. The valve assembly selectively closes the passageway and includes a valve body and a valve seat structure. The valve body has opposing first and second ends and an internal chamber. The valve body has a circular base and a wall. The circular base has leading and trailing sides, wherein the leading side defines the first end of the valve body. The wall extends from the trailing side of the base to form a dome-like shape terminating at the second end. A slit is formed through a thickness of the wall and open to the chamber at the second end. The wall defines opposing sealing edges at the slit. The valve seat structure forms along the conduit and sealingly maintains the base. The valve seat structure has an upper circumferential surface and a lower circumferential surface. The upper circumferential surface engages the leading side of the base. The lower circumferential surface engages the trailing side of the base. At least one of the upper and lower surfaces forms a segment of increased height. Upon final assembly, the valve body is disposed across the passageway with the slit providing a selectively openable path through the valve assembly, and a force imparted by the segment of increased height flexing the base and biasing the opposing sealing edges into engagement.

BRIEF DESCRIPTION OF THE DRAWINGS

FIGS. 2A and 2B are cross-sectional views of an airway access adapter assembly portion of the apparatus of FIG. 1;

FIG. 6A is a side view of valve body useful with a valve device component the apparatus of FIG. 1;

FIG. 6B is a top view of the valve body of FIG. 6A;

FIG. 6C is a bottom view of the valve body of FIG. 6A;

FIG. 6D is a cross-sectional view of the valve body of FIG. 6A;

DETAILED DESCRIPTION

Figure 1:
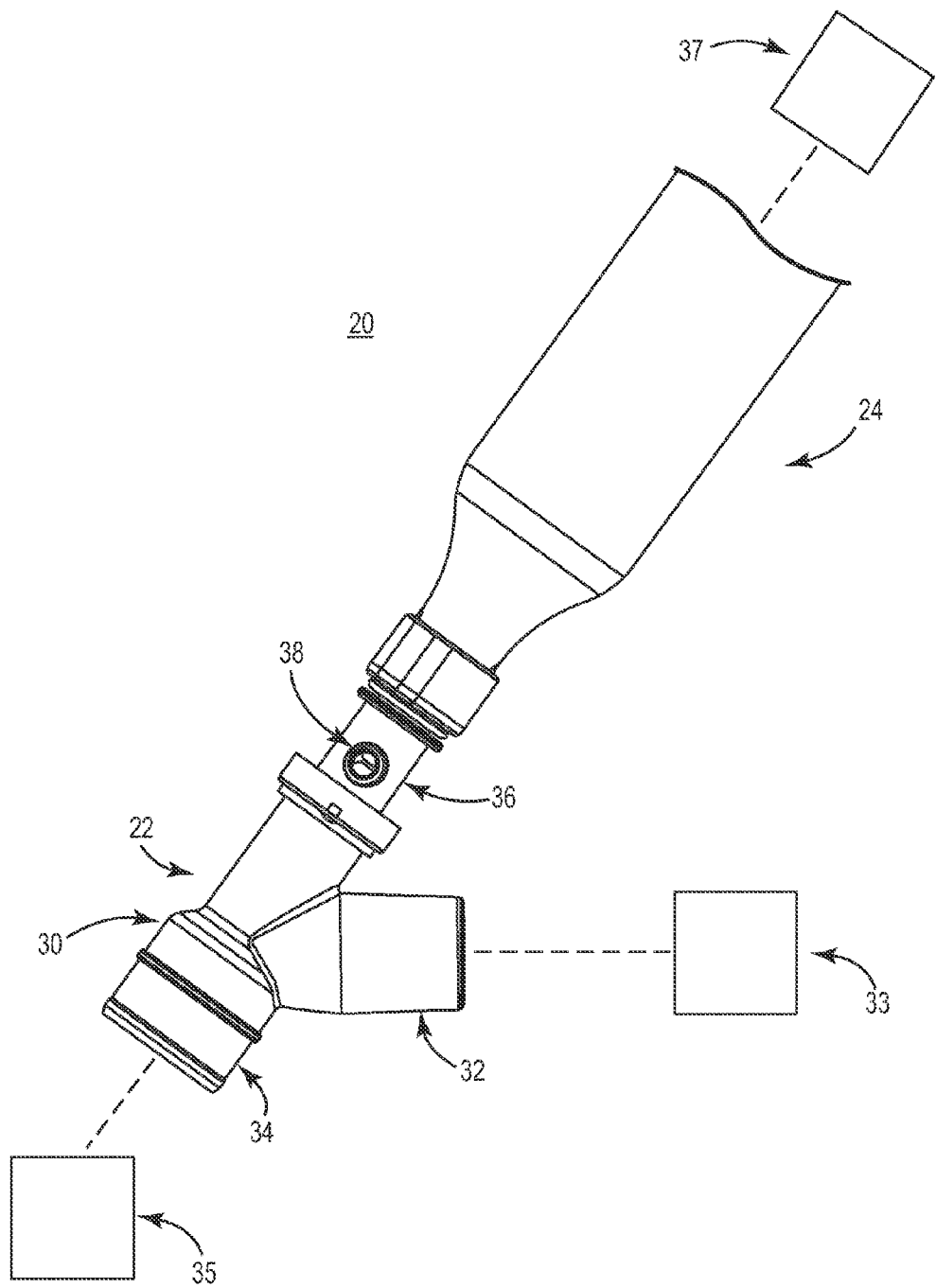
FIG. 1 is a side view of a respiratory apparatus in accordance with aspects of the present disclosure.

Some aspects in accordance with the present disclosure relate to an airway access adapter for use in a ventilator circuit, along with a closed suction catheter assembly useful with the airway access adapter. With this in mind, one embodiment of a respiratory apparatus 20 is illustrated in FIG. 1, and includes an airway access adapter assembly (or "adapter assembly") 22 and a closed suction catheter assembly 24. Details on the various components are provided below. In general terms, however, the adapter assembly 22 is configured for placement within a patient breathing circuit (not shown), fluidly interconnecting an artificial airway (not shown) that is otherwise in direct fluid communication with a patient's respiratory tract (e.g., via an endotracheal tube, tracheostomy tube, etc.) with a source of mechanical ventilation (e.g., tubing connected to a ventilator). Further, the adapter assembly 22 facilitates removable insertion of instruments into the breathing circuit, including the suction catheter assembly 24. To this end, the adapter assembly 22 and the suction catheter assembly 24 incorporate corresponding features that promote cleaning of the suction catheter assembly 24 while the suction catheter assembly 24 remains attached to the adapter assembly 22.

With the above in mind, the adapter assembly 22 includes a manifold housing 30 forming or providing a ventilator port 32, a respiratory port 34, an access port 36 and a flush port 38. As best shown in FIGS. 2A and 2B, the housing 30 fluidly interconnects the ports 32-38, and the adapter assembly 22 further includes a valve device 40 adjacent the access port 36.

The ventilator port 32 is illustrated in FIG. 2A, and is configured for fluid connection to a ventilator 33 (FIG. 1), for example via tubing. In this regard, the adapter assembly 22 can include additional components useful in establishing and maintaining the desired fluid connection, such as a swivel-type coupling, a seal, etc.

The respiratory port 34 is configured for fluid connection to an artificial airway 35 (FIG. 1) otherwise establishing a direct connection to the patient's respiratory tract. For example, the respiratory port 34 can be connected to tubing that in turn is fluidly connected to an endotracheal tube or a tracheostomy tube; alternatively, the artificial airway 35 can be directly connected to the respiratory port 34. Further, the adapter assembly 22 can include additional components useful in establishing and maintaining the desired fluid connection, such as a swivel-type coupling, a seal, etc.

Regardless of an exact construction of the ventilator port 32 and the respiratory port 34 and/or related components such as couplings or seals, the housing 30 fluidly interconnects the ports 32, 34. With this construction, then, the adapter assembly 22 can be inserted into a patient breathing circuit and maintain a necessary fluid connection between the ventilator 33 and the patient's respiratory tract.

The access port 36 is configured to allow selective insertion of various instruments into the housing 30, and in particular to (and optionally through) the respiratory port 34. Thus, in some embodiments, the access port 36 is axially aligned with the respiratory port 34. With specific reference to FIG. 2B, the access port 36 includes or defines a conduit 42 establishing a passageway 44. The passageway 44 is open at a proximal or insertion end 46 of the access port 36, with the insertion end 46 including a flange 48 extending radially outwardly from the conduit 42 in some embodiments. Regardless, an inner surface 50 of the conduit 42 defines a cross-sectional area of the passageway 44 that is sized in accordance with one or more instruments commonly used in conjunction with the adapter assembly 22, including the suction catheter assembly 24 as described below.

The flush port 38 projects from the conduit 44 adjacent the insertion end 46, and is fluidly connected to the passageway 44. More particularly, the flush port 38 forms a channel 52 extending between, an open relative to, an inlet 54 and an outlet 56. The flush port 38 can include various features at the inlet 54 that promote fluid connection to tubing or other components associated with a source of liquid such as water or saline (not shown) useful for cleaning (or "flushing") a body inserted into the access port 36. For example, a barbed surface 58 is optionally formed. Regardless, the outlet 56 is formed through or at the interior surface 50 of the conduit 42 at a known or predetermined longitudinal position or distance relative to the insertion end 46. As described below, the predetermined location of the outlet 56 relative to the insertion end 46 corresponds with a dimensional attribute of the suction catheter system 24 (FIG. 1) to better ensure that liquid introduced at the flush port 38 interfaces with the suction catheter system 24 at a desired location.

As a point of reference, FIGS. 2A and 2B illustrate the access port 36 as being formed by first and second frame or housing portions 60, 62. The first frame portion 62 is an integrally formed structure of the manifold 30 (i.e., the first frame portion 62 is integrally formed with the ventilator port 32 and the respiratory port 34), with the second frame portion 60 defining the insertion end 46. With this construction, the second frame portion 60 is assembled to the first frame portion 62 to complete the access port 36, as well as to complete the valve device 40. In other embodiments, however, the access port 36 is a homogeneous body, and does not incorporate two (or more) separable parts. Regardless, the valve device 40 extends across and fluidly seals the passageway 44, and incorporates features that permit selective insertion of an instrument through the access port 36. Upon removal of the instrument, the valve device 40 operates to fluidly seal the passageway 44 (i.e., seals the insertion end 46 from the ventilator port 32 and the respiratory port 34). One optional construction of the valve device 40 is described in greater detail below. In more general terms, the valve device 40 can assume a variety of forms useful in facilitating sealed insertion and removal of instruments through the access port 36 (e.g., check valve, duck valve, flapper valve, etc.).

Figure 3:
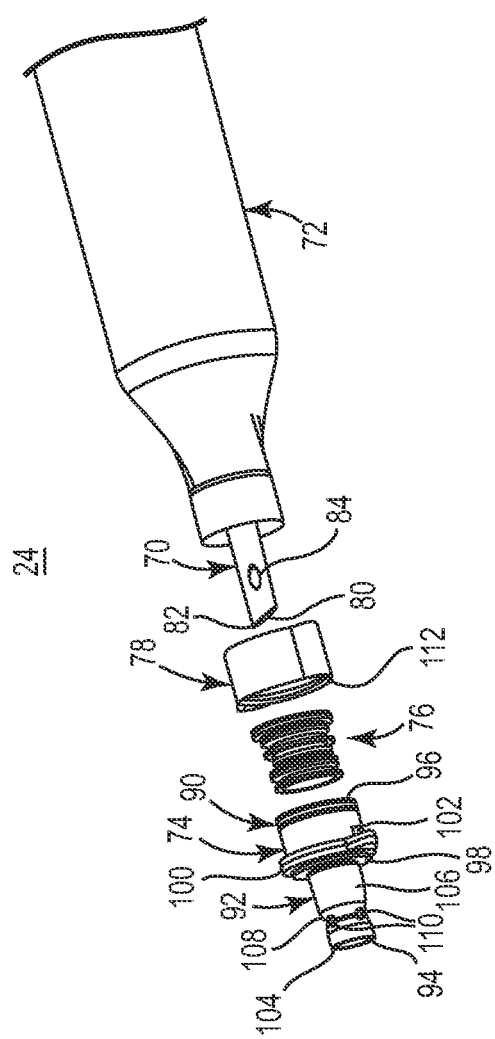
FIG. 3 is an exploded, perspective view of a portion of a closed section catheter assembly component of the apparatus of FIG. 1.

As indicated above, and returning to FIG. 1, the suction catheter assembly 24 is configured for use with the adapter assembly 22 via the access port 36. With this in mind, one construction of the suction catheter assembly 24 in accordance with the present disclosure is shown in greater detail in FIG. 3, and includes a catheter 70, a flexible sheath 72, a fitting 74, a seal body 76, and a coupler 78. Details on the various components are provided below. In general terms, however, the catheter 70 is slidably assembled to the fitting 74 via the seal body 76. Similarly, the flexible sheath 72 is mounted to the fitting 74 via the coupler 78. Finally, the fitting 74 is configured to interface with the access port 36 (FIG. 1) to permit insertion of the catheter 70 through the adapter assembly 22 (FIG. 1), as well as cleaning of the catheter 70.

The catheter 70 can assume a variety of forms currently known, or in the future developed, useful for performing suction procedures on a patient otherwise connected to the breathing circuit. Thus, in some embodiments, the catheter 70 defines one or more lumens 80 (referenced generally) through a length thereof, extending from an opening at a distal end 82. A side opening 84 can further be formed that is open to the lumen 80. With this configuration, the distal end 82 may be extended through the artificial airway 35 (FIG. 1) and into the respiratory tract of the patient (e.g., the patient's lungs). The lumen 80 is similarly open at a proximal end (not shown) of the catheter 70, that in turn can be connected to a vacuum source 37 (FIG. 1). Upon placement of the distal end 82 in the patient's respiratory tract and activation of the vacuum source 37, respiratory secretions in the patient and in the artificial airway 35 can be removed.

The flexible sheath 72 surrounds the catheter 70 apart from the fitting 74, and serves to contain and isolate contaminants and mucus that may accumulate on the catheter 70 as it is withdrawn from the respiratory tract. In addition, the sheath 72 protects external contaminants from contacting the catheter 70. The sheath 72 can assume any form useful for closed suction catheter applications, and is typically formed of a thin-walled plastic.

The fitting 74 includes a hub 90 and a nose 92, and defines a continuous lumen 94 (referenced generally in FIG. 3) extending longitudinally therethrough. The fitting 74 can be formed from a rigid, surgically safe material such as stainless steel, plastic, ceramic, etc.

The hub 90 is sized to receive the seal body 76 and the coupler 78, and to interface with the access port 36 (FIG. 1) as described below. With this in mind, the hub 90 is defined by opposing, first and second ends 96, 98, with the second end 98 having a diameter corresponding with a dimensional attribute of the access port 36 to ensure a desired arrangement of the fitting 74 relative to the access port 36 upon final assembly. In some embodiments, the hub 90 includes a flange 100 maintaining one or more pins 102 adapted to achieve a mounted relationship with corresponding features of the coupler 78, although a wide variety of other mounting techniques are equally acceptable.

The nose 92 is a tubular body extending from second end 98 of the hub 90, and terminates at a trailing end 104. The lumen 94 is open at the trailing end 104, with the nose 92 sized for insertion into the access port 36 (FIG. 1). The nose 92 forms an exterior surface 106 defining a slightly tapering outer diameter (i.e., from the second end 98 of the hub 90 to the trailing end 104) in some embodiments. In addition, the nose 92 forms a circumferential groove 108 along the exterior surface 106 adjacent the trailing end 104, and one or more apertures 110. The groove 108 can be an undercut machined into the exterior surface 106 during manufacture of the fitting 74. The apertures 110 extend through a thickness of the nose 92, establishing a fluid pathway between the exterior surface 106 and the lumen 94. In some embodiments, four of the apertures 110 are formed in an equidistantly spaced fashion and are identical in size and shape. Alternatively, any other number of the apertures 110 (greater or lesser) is acceptable and/or the apertures 110 need not be identical. Regardless, the aperture(s) 110 are formed within a region of the groove 108.

Figure 4:
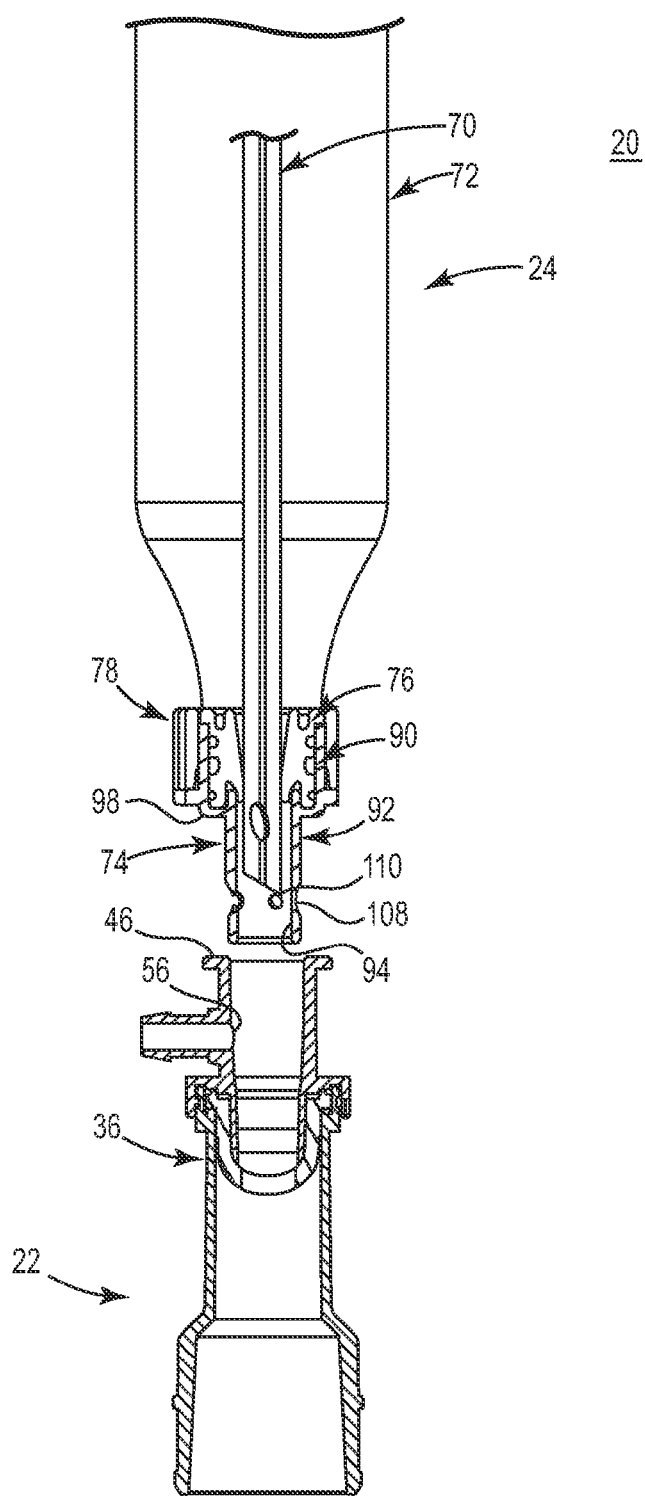
FIG. 4 is an exploded, cross-sectional view of the apparatus of FIG. 1.

A relationship of the groove 108 and the apertures 110 is further reflected in the view of FIG. 4. As shown, the apertures 110 are circumferentially spaced within the groove 108 (e.g., centered relative to a longitudinal height of the groove 108), and are open to the lumen 94. Further, the groove 108 (and thus the apertures 110) is located at a known or predetermined longitudinal distance relative to the second end 98 of the hub 92. As made clear below, this known relationship corresponds with the known relationship of the flush port outlet 56 relative to the insertion end 46 of the access port 36 so as to position the groove 108 in fluid communication with the outlet 56 upon final assembly.

With continued reference to FIG. 4, the seal body 76 is maintained within the hub 90, and is sized to contact, and seal against, the catheter 70. The seal body 76 can assume a variety of forms and constructions, and can incorporate various features that enhance mounting within the hub 90. Regardless, the seal body 76 exhibits at least a degree of deformability, thereby permitting sliding of the catheter 70 relative to the seal body 76 while maintaining a fluidly sealed relationship. In some embodiments, the seal body 76 provides a wiping-type attribute, whereby contaminants accumulated on the exterior surface of the catheter 70 are removed by the seal body 76 as the catheter 70 is withdrawn therethrough.

The coupler 78 is mountable to the hub 90, and serves to lock the sheath 72 against the hub 90 as reflected in FIG. 4. Thus, the coupler 78 can have a variety of constructions differing from those shown, and may include one or more bores 112 (FIG. 3) sized to receive the pins 102 (FIG. 3) in some embodiments.

Figure 5A:
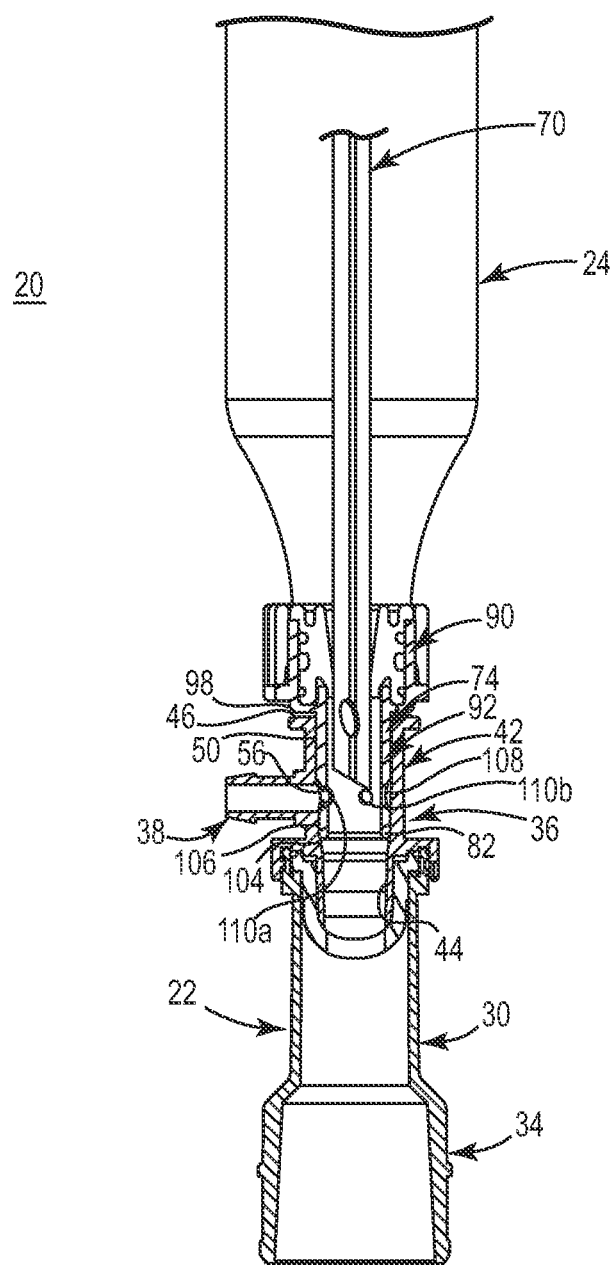
FIGS. 5A and 5B are cross-sectional views of the apparatus of FIG. 1.

Connection between the adapter assembly 22 and the suction catheter assembly 24 is shown in FIG. 5A. The nose 92 is inserted into the access port 36 via the insertion end 46 (e.g., slip fit mounting), thereby establishing a pathway for the catheter 70 relative to the passageway 44. With this arrangement, the distal end 82 of the catheter 70 can be distally advanced through the manifold 30 and into and through the respiratory port 34 for performing a respiratory tract suctioning procedure as described above. In this regard, and as better reflected in FIG. 5B, the valve device 40 provides one or more features (such as a slit 120) that permits passage of the catheter 70 while effectuating re-sealing of the passageway 44 once the catheter 70 is withdrawn.

Returning to FIG. 5A, a clinician may periodically wish to clean or flush the catheter 70, for example the distal end 82, via the flush port 38. In this regard, the access port 36 and the fitting 74 are configured such that upon insertion of the nose 92 to the position of FIG. 5A, the circumferential groove 108 is aligned with the flush port outlet 56. For example, and as alluded to above, a longitudinal distance between the groove 108 and the second end 98 of the hub 90 corresponds with a longitudinal distance between the flush port outlet 56 and the insertion end 46 of the access port 36 such that when the second end 98 is placed into abutment with the flange 48 of the insertion end 46 (i.e., the second end 98 has an outer dimension or diameter greater than a corresponding dimension of the passageway 44 at the insertion end 46), the flush port outlet 56 and the groove 108 are aligned. Notably, a variety of other configurations can additionally or alternatively be employed to effectuate this aligned relationship (as well as temporarily locking the fitting 74 to the access port 36). For example, a diameter of the passageway 44 can taper to a dimension less than an outer diameter of the nose 92 at the trailing end 104 at predetermined longitudinal location relative to the flush port outlet 56 that correlates with a longitudinal distance between the trailing end 104 and the groove 108. Regardless, the inner surface 50 of the conduit 42 and the exterior surface 106 of the nose 92 have corresponding shapes and dimensions (e.g., corresponding longitudinal taper) such that in the assembled position of FIG. 5A, the exterior surface 106 of the nose 92 nests against the inner surface 50 of the conduit 42.

The aligned relationship between the flush port outlet 56 and the groove 108 establishes a fluid connection with the apertures 110. More particularly, a seal-like relationship is formed between the inner surface 50 of the conduit 42 and the exterior surface 106 of the nose 92. The groove 108 effectively defines a gap or spacing within this nested interface that fluidly interconnects each of the apertures 110 with the flush port outlet 56. Thus, for example, the plurality of apertures 110 can include a first aperture 110a and a second aperture 110b. In some arrangements, at least one of the apertures 110 (e.g., the second aperture 110b with respect to the one representation of FIG. 5A) is not directly aligned with the flush port outlet 56. Liquid entering the flush port channel 52 is forced to the outlet 56 and then into the groove 108. The groove 108 directs the so-delivered liquid to each of the apertures 110, including ones of the apertures 110 that are not directly aligned with the outlet 56 (e.g., liquid is delivered to the second aperture 110b via the groove 108). As a point of reference, with a catheter flushing procedure, the catheter 70 can first be withdrawn relative to the fitting 74 such that the distal end 82 is proximate the apertures 110 so as to better ensure that the delivered cleaning liquid interfaces with the distal end 82 and can be evacuated through the catheter lumen 80.

In addition to forming the respiratory apparatus 20, the adapter assembly 22 can be used in conjunction with other instruments as desired by a clinician. For example, the suction catheter assembly 24 can be disconnected from the access port 36, and a different instrument (e.g., bronchoscope) inserted therein. Under these circumstances, the flush port 38 remains with the adapter assembly 22, and is therefore available to perform a cleaning procedure relative to this separate instrument.

As mentioned above, the valve device 40 is provided to maintain a fluidly sealed relationship of the access port 36, while permitting periodic insertion of an instrument therethrough. In some embodiments, the valve device 40 incorporates features that enhance sealing surface closure.

Figure 5B:
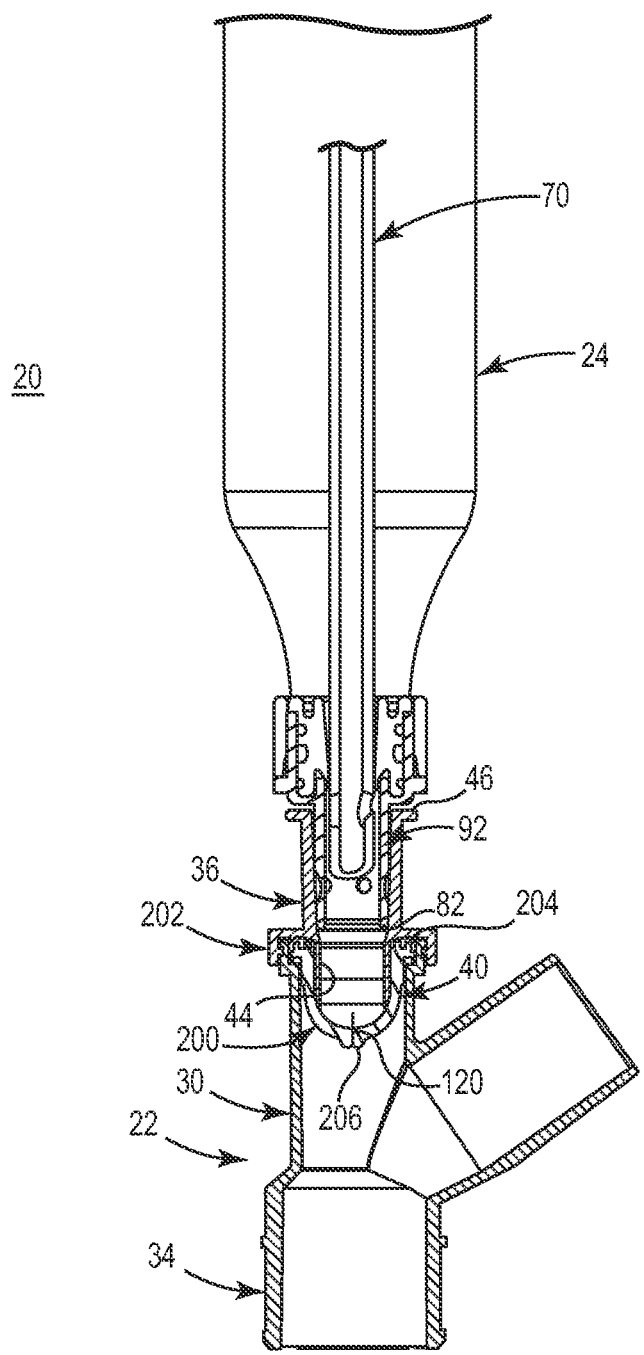

For example, the valve device 40 can include a valve body 200 and a valve seat structure 202 (referenced generally in FIG. 5B). In general terms, the valve seat structure 202 maintains the valve body 200 relative to the passageway 44, with the components 200, 202 configured in tandem to provide the enhanced sealing. Relative to final assembly within the passageway 44, the valve body 202 can be described as having or defining a first or upstream end 204 and a second or downstream end 206. The upstream end 204 is located more proximate the insertion end 46 of the access port 36 as compared to the downstream end 206.

The valve body 200 is shown in greater detail in FIGS. 6A-6C and includes a base 210 and a wall 212. The wall 212 extends from the base 210 to define an internal chamber 214 (referenced generally in FIG. 6B), and has a dome-like shape. The valve body 200 can be formed from a variety of flexible, elastically deformable materials appropriate for effectuating a fluid-tight seal, such as rubber.

The base 210 is circular or ring-like, and defines a leading side 216 and a trailing side 218. Relative to the final assembled position (FIG. 5A), then, the leading side 216 forms the upstream end 204. The sides 216, 218 are configured for engagement with corresponding features of the valve seat structure 202 (FIG. 5A). In this regard, and as described below, the base 210 is caused to asymmetrically flex or deflect in connection with engaged mounting to the valve seat structure 202. In some embodiments, to enhance this desired flexation, the base 210 can include one or more fingers 220, formed as tapered projections at or from the leading side 216 shown in FIGS. 6A and 6B. An arrangement and configuration of the fingers 220 relative to other features of the valve body 200 and the valve seat structure 202 is made clear below. In addition, and as shown in FIG. 6D, a slot 222 can be formed along the trailing side 218, resulting in a circumferential rib 224, with the slot 222/rib 224 providing additional surface area interface with the valve seat structure 202.

With continued reference to FIG. 6D, the wall 212 projects from the trailing side 218 of the base 210, terminating at a tip 226. The tip 226 defines the downstream end 206 (FIG. 5A) of the valve body 200, and is generally closed relative to the internal chamber 214. Passage through the tip 226 (and thus through the chamber 214) is provided via a slit 230 (e.g., akin to the slit 120 of FIG. 5B) formed through a thickness of the wall 212 (i.e., extending through an interior face 232 and an exterior face 234 of the wall 212). As best shown in FIGS. 6B and 6C, the slit 230 is centered relative to the base 210, and is highly linear or planar. For reasons made clear below, the optional fingers 220 are positioned perpendicular to a plane of the slit 230 as reflected in FIG. 6B.

FIG. 6D illustrates that the slit 230 effectively divides the tip 226 into two halves, with each half forming a sealing edge 240 (one of which is shown in FIG. 6D) along the slit 230. When subjected to a desired flexation or biasing force, the sealing edges 240 are forced into more intimate contact with one another, especially along the exterior face 234, thereby effectuating a more complete seal. Thus, the sealing edges 240 can be forced apart by an instrument (not shown) being inserted through the slit 230, but will readily and repeatedly return to a sealed relationship upon removal of the instrument. In some embodiments, to further promote this natural, sealed arrangement, a thickness of the wall 212 is elevated in a region of the slit 230. For example, the wall 212 can be described as defining a first portion 242 extending from the base 210, and a second portion 244 extending from the first portion 242, with the second portion 244 defining the tip 226. With these designations in mind, a thickness of the wall 212 at the tip 226 is greater than a thickness of the wall 212 along the first portion 242. The elevated thickness along the slit 230 is further illustrated in FIG. 6A by formation of a ridge 246.

Figure 7:
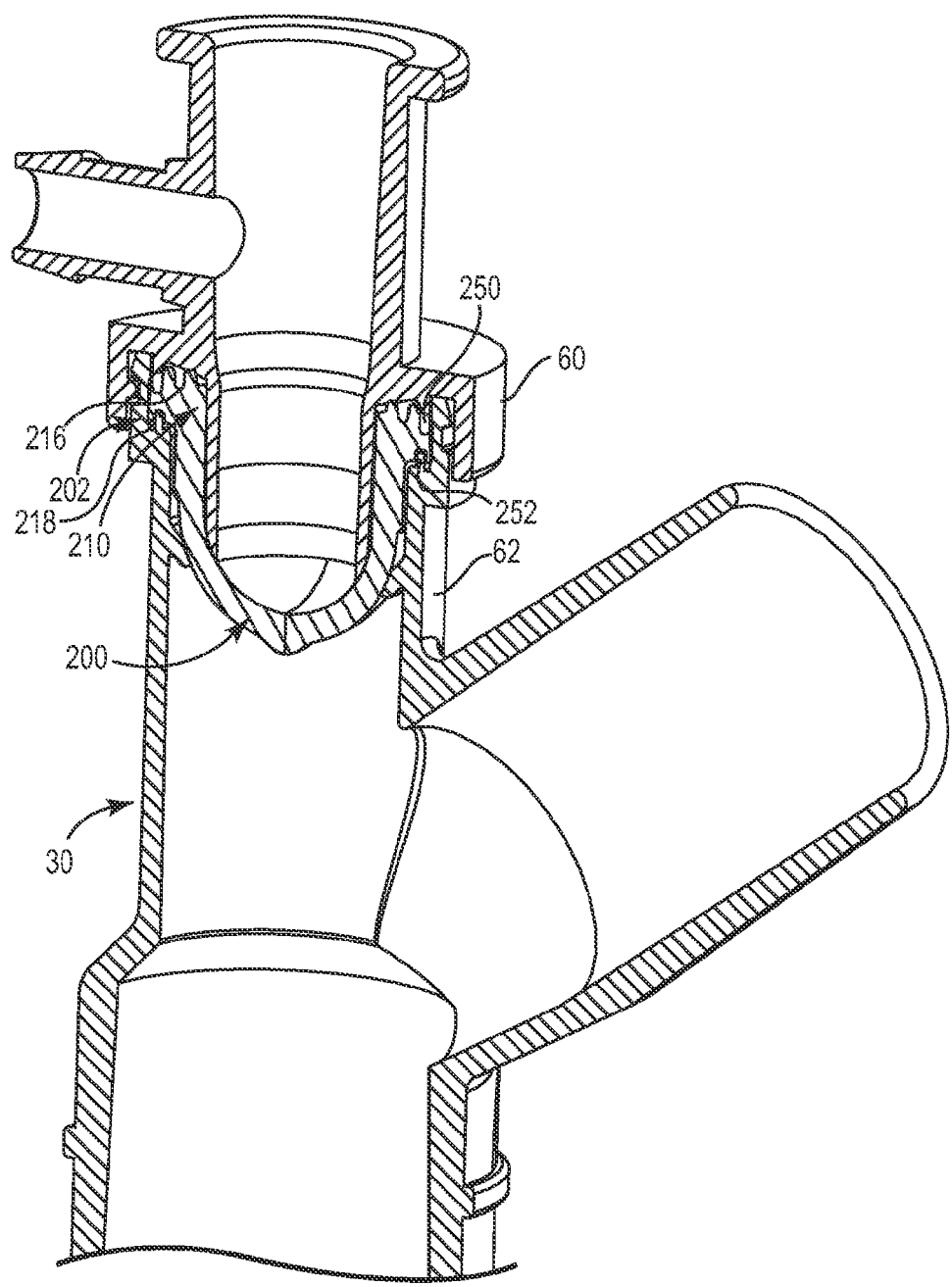
FIG. 7 is a cross-sectional view of a portion of an airway access adapter including a valve device in accordance with aspects of the present disclosure.

With the above construction of the valve body 200 in mind, the valve seat structure 202 can be described with initial reference to FIG. 7. The valve seat structure 202 is provided, in some embodiments, as part of the manifold housing 30, and includes an upper circumferential surface 250 and a lower circumferential surface 252. The upper surface 250 is configured to engage the leading side 216 of the base 210, whereas the lower surface 252 is configured to engage the trailing side 218. In this regard, one or both of the surfaces 250, 252 incorporate features that impart a flexation or biasing force upon the base 210.

Figure 8A:
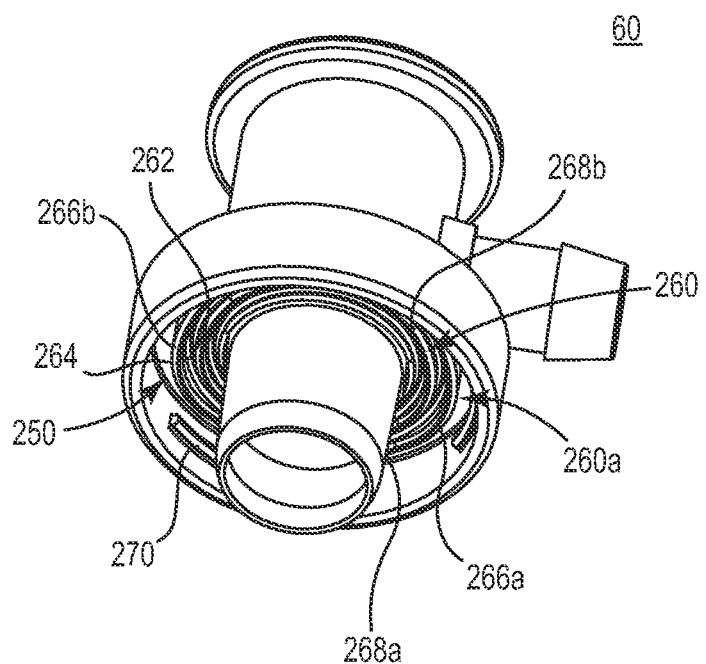
FIG. 8A is a perspective view of a component of the valve device of FIG. 7, illustrating a portion of a valve seat structure.
Figure 8C:
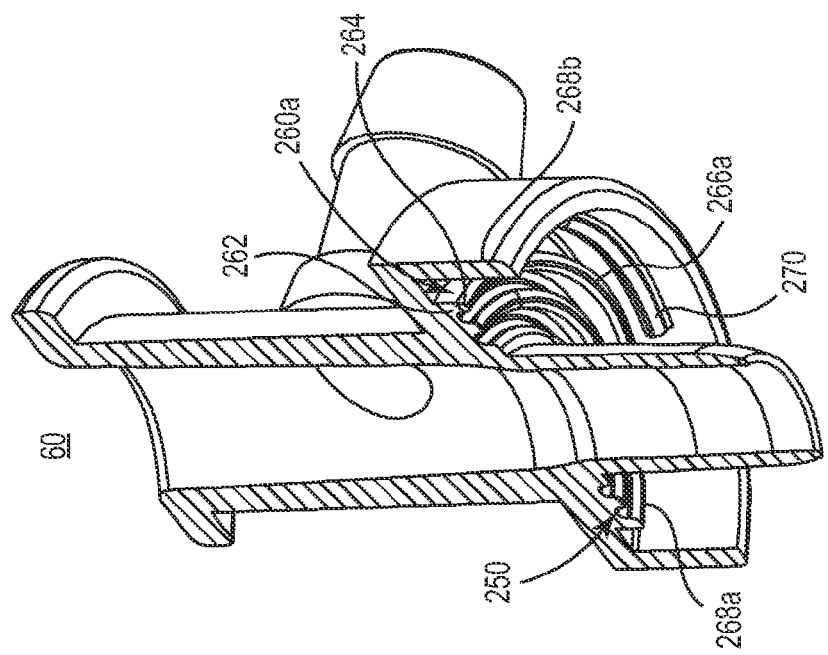
FIGS. 8B and 8C are cross-sectional views of the component of FIG. 8A.
Figure 8B:
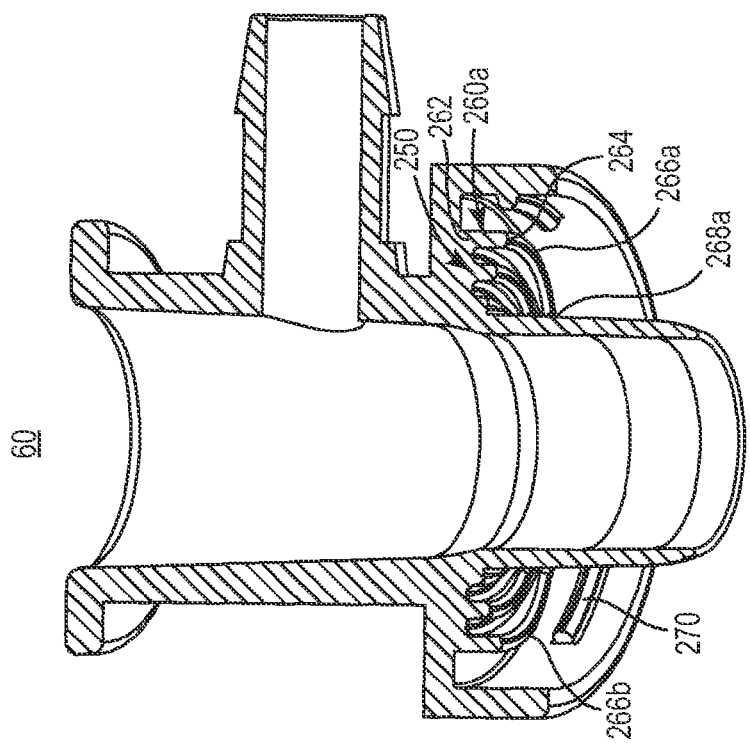

In some embodiments, the upper and lower surfaces 250, 252 are formed by separable parts of the manifold housing 30, for example the first and second frame portions 60, 62, respectively, as mentioned above. With this in mind, FIGS. 8A-8C shows the first frame portion 60 removed from a remainder of the manifold 30, and illustrates the upper surface 250 in greater detail. More particularly, the upper surface 250 includes or forms one or more circumferential shoulders 260 each having at least one segment of increased height. For example, a first shoulder 260a can be described as extending from a bottom side 262 to an engagement face 264. A dimension of this extension defines a height of the shoulder 260a. With these conventions in mind, the first shoulder 260a varies in height along the circumference thereof, for example defining first and second raised segments 266a, 266b, and first and second lowered segments 268a, 268b. The raised segments 266a, 266b are circumferentially spaced from one another via the lowered segments 268a, 268b, with the raised segments 266a, 266b having an increased height as compared to the lowered segments 268a, 268b. As a point of reference, FIG. 8B illustrates the shoulder 260a tapering in height from the raised segments 266a, 266b to the first lowered segment 268a, whereas FIG. 8C illustrates the shoulder 260a increasing in height from the lowered segments 268b, 268b to the first raised segment 266a. A spatial location of the raised segments 266a, 266b relative features of the valve body 200 (FIG. 7) upon final assembly is described below, clarifying biasing or flexation in the valve body 200 due to the existence of the raised segments 266a, 266b.

As a point of reference, FIGS. 8A-8C illustrate the upper surface 250 as having three of the shoulders 260 (with each of the shoulders 260 having raised segments that are radially aligned with one another). Alternatively, a greater or lesser number of the shoulders 260 can be provided. Further, the first frame portion 60 can include additional features that facilitate mounting of the valve body 200 (FIG. 7), such as radial projections 270.

Figure 9A:
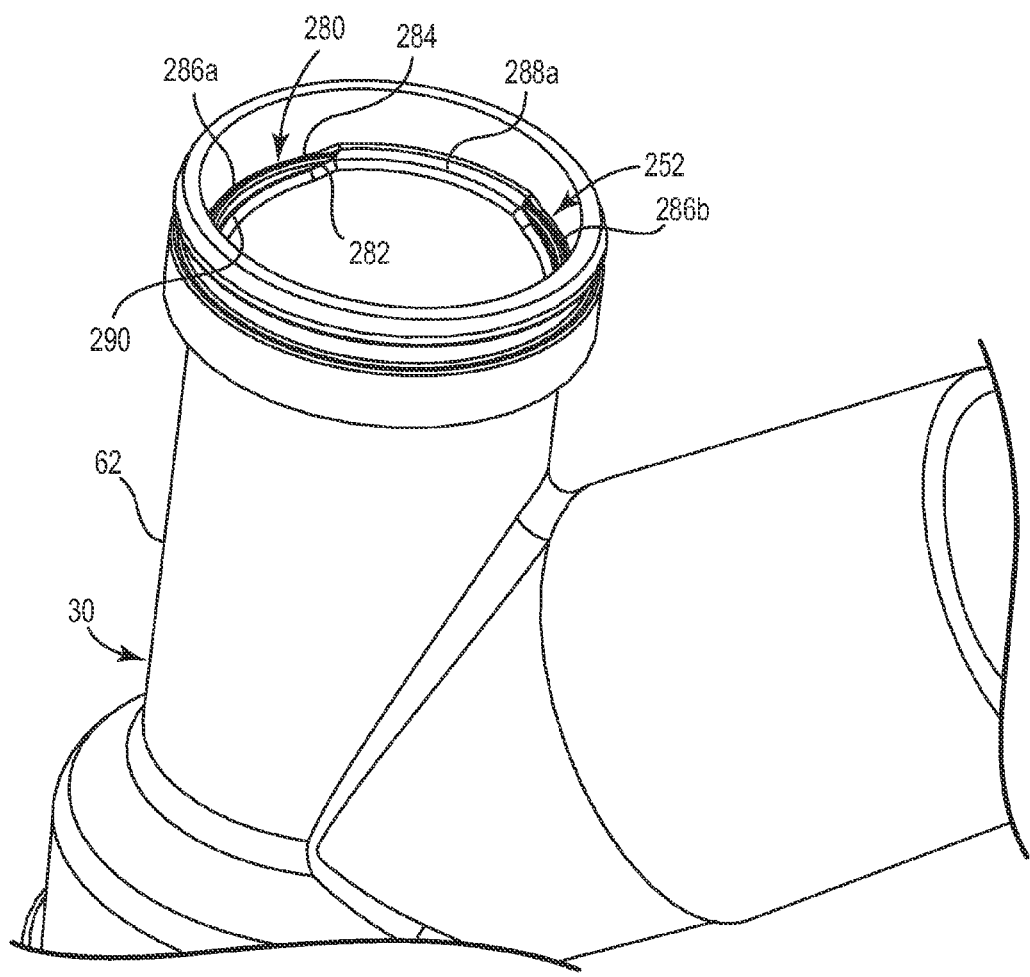
FIG. 9A is an enlarged, perspective view of another component of the valve device of FIG. 7.
Figure 9C:
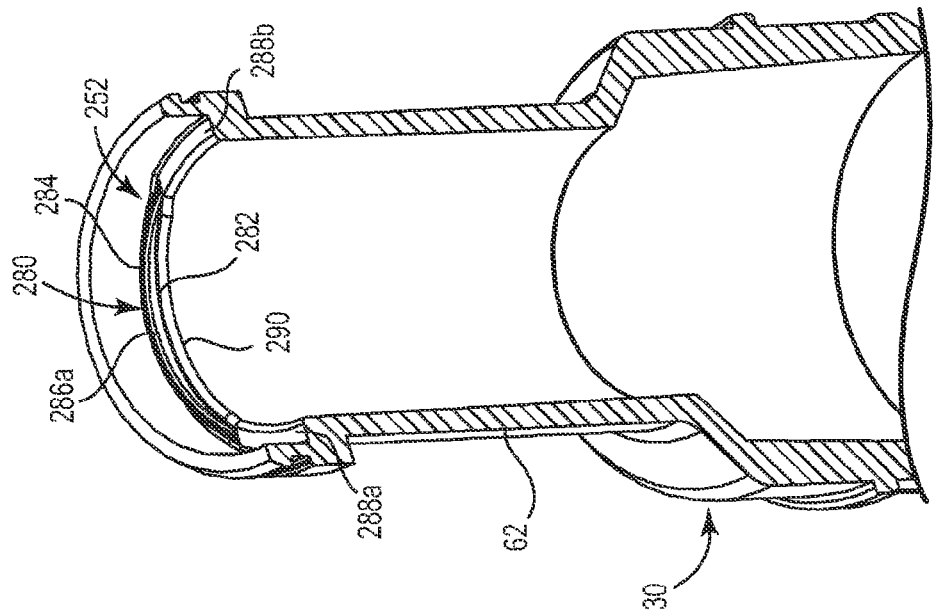
FIGS. 9B and 9C are cross-sectional views of the component of FIG. 9A.
Figure 9B:
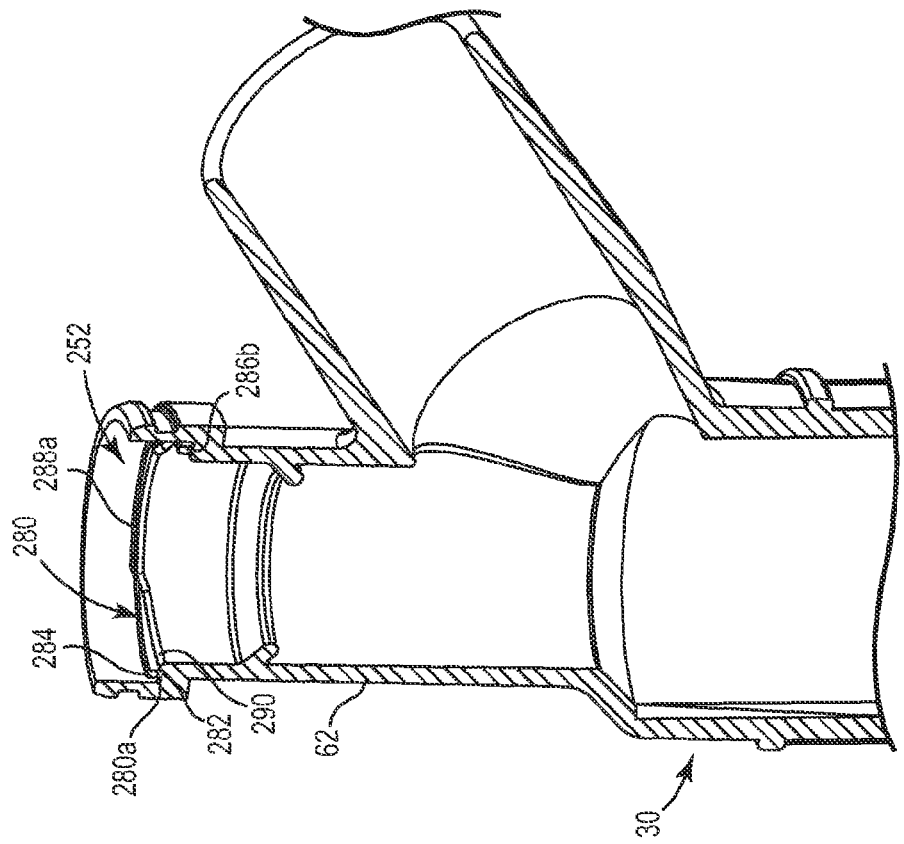

The lower surface 252 can include similar features as shown in FIGS. 9A-9C (that otherwise illustrate a portion of the manifold 30 with the first frame portion 60 removed). The lower surface 252 includes or is defined by a circumferential rib 280, with the rib 280 having a varying height. More particularly, the rib 280 extends from a bottom 282 to an engagement face 284, with the distance of extension defining the height of the rib 280. With this in mind, the rib 280 can be described as defining first and second raised segments 286a, 286b, and first and second lowered segments 288a, 288b. The raised segments 286a, 286b are circumferentially spaced from one another by the lowered segments 288a, 288b, with the raised segments 286a, 286b having an elevated height as compared to the lowered segments 288a, 288b. As a point of reference, FIG. 9B illustrates the rib 280 tapering in height from the first and second raised segments 286a, 286b to the first lowered segment 288a. Conversely, FIG. 9C illustrates the rib 280 increasing in height from the first and second lowered segments 288a, 288b to the first raised segment 286a. A spatial location of the raised segments 286a, 286b relative features of the valve body 200 (FIG. 7) upon final assembly is described below, clarifying biasing or flexation in the valve body 200 due to the existence of the raised segments 286a, 286b. Additional features can further be incorporated that enhance the desired interface with the valve body 200, for example a radial, convex undercut 290 formed along the raised segments 286a, 286b.

Figure 10A:
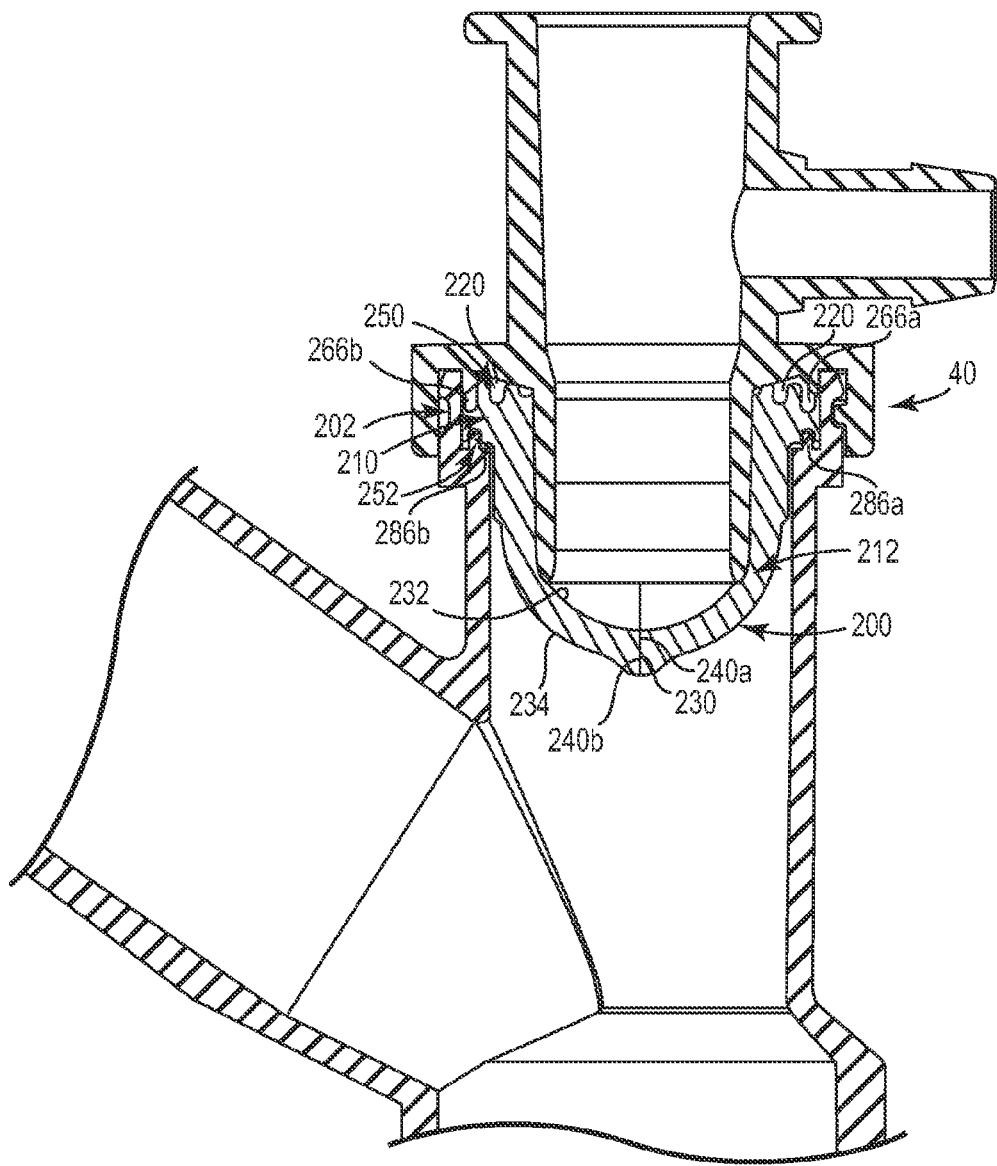
FIGS. 10A and 10B are cross-sectional views of the airway access adapter of FIG. 7 upon final assembly.
Figure 10B:
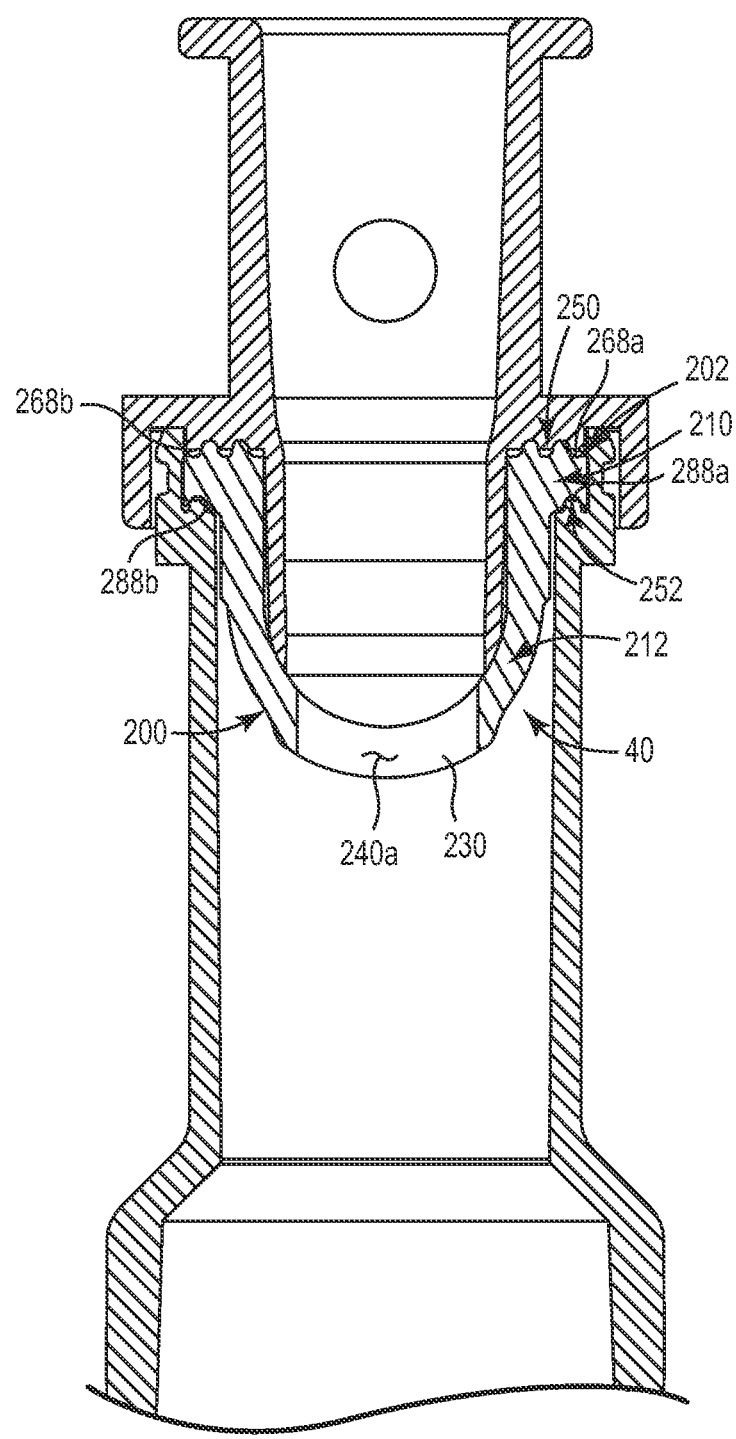

Final assembly of the valve device 40 is shown in FIGS. 10A and 10B. The valve body 200 is mounted to the valve seat structure 202 via pinched engagement of the base 210 between the upper and lower surfaces 250, 252. In this regard, the increased height features of the surfaces 250, 252 are longitudinally aligned. For example, and with specific reference to FIG. 10A, the first raised segment 266a of the upper surface 250 is longitudinally aligned with the first raised segment 286a of the lower surface 252; similarly, the second raised segments 266b, 286b are also longitudinally aligned. Notably, the valve body 200 is arranged such that the raised segments 266a/286a, 266b/286b are generally parallel with a plane of the slit 230 for reasons made clear below.

At the region of interface of the raised segments 266a/286a and 266b/286b, an increased compression force is imparted on to the corresponding portion of the base 210 (as compared to the compression force imparted on to the base 210 at regions corresponding with the lowered segments 268a/288a and 268b/288b interface illustrated in FIG. 10B). The base 210, in turn, flexes in response to this asymmetrical bias, effectively transferring a "pushing" type force or bias on to the exterior face 234 of the wall 212 and a "pulling" type force or bias on to the interior face 232. In other words, because the valve seat structure 202 imparts a non-uniform force on to the base (due to the non-uniform heights of the corresponding surfaces 250, 252), the transmitted forces cause the wall 212 to "pucker" or flex in a plane of the slit 230. This effect is further enhanced by the optional fingers 220; as shown, the valve body 200 is arranged such that the fingers 220 are located at the raised segment 266a/286a, 266b/286b interfaces, increasing the biasing or puckering force imparted on to the base 210.

Due to the above-described non-uniform flexing of the base 210, the opposing sealing edges 240a, 240b at the slit 230 are self-biased to a tightly sealed relationship, with the biasing being more focused at the exterior face 234. In other words, relative to the plane of the view of FIG. 10A, the biasing forces imparted on to the valve body 200 are parallel to a plane of the slit 230. Conversely, and relative to the plane of the view of FIG. 10B, the asymmetrical valve seat structure 202 does not cause or force pressure changes in a direction perpendicular to the sealing edge 240a shown.

The above construction of the valve device 40 represents a marked improvement over previous valve configurations employed with airway access adapters. A more consistent, long-term seal is provided, yet desired insertion and withdrawal of instruments through the valve device 40 can occur. Notably, this same valve device construction can be employed with alternative airway access adapters that do not otherwise incorporate the closed suction catheter assembly interface features described above. Similarly, the benefits provided with the respiratory apparatus (e.g., flushing of a connected suction catheter) can be achieved with entirely different valve device constructions.

Although the present disclosure has been described with respect to preferred embodiments, workers skilled in the art will recognize that changes can be made in form and detail without departing from the spirit and scope of the present disclosure.

What is claimed is:

1. An adapter assembly comprising:
   a manifold comprising and fluidly interconnecting a ventilator port, a respiratory port, and an access port having a circumferential cross section, the access port comprising a valve seat that has an upper circumferential surface and a lower circumferential surface; and
   a valve assembly coupled to the access port, the valve assembly comprising a circular base with a substantially planar upper surface in contact with the upper circumferential surface of the valve seat and a lower surface in contact with the lower circumferential surface of the valve seat and a wall extending from the base with a slit that is formed through the wall with opposing sealing edges, wherein two circumferentially discontinuous portions are on the upper surface at opposing sides of the slit, each forming a segment of increased height from the planar surface, the discontinuous portions contact the upper circumferential surface of the valve seat and bias the opposing sealing edges into engagement.

2. The adapter assembly of claim 1, wherein the segment of increased height is positioned perpendicular to a plane of the slit.

3. The adapter assembly of claim 1, wherein
   the manifold comprises a first frame portion having an upper surface and a second frame portion having a lower surface; and
   the base is captured between the upper and lower surfaces of the first and second frame portions.

4. The adapter assembly of claim 3, wherein the lower surface of the second frame portion comprises a rib having circumferentially spaced, first and second raised segments that cause the base to more overtly flex at regions in contact with the raised segments.

5. The adapter assembly of claim 4, wherein the upper surface of the first frame portion comprises a shoulder having circumferentially spaced first and second raised segments that cause the base to more overtly flex at regions in contact with the raised segments of the upper circumferential surface.

6. The adapter assembly of claim 5, wherein upon final assembly, the raised segments of the lower surface of the second frame portion are longitudinally aligned with respective ones of the raised segments of the upper surface of the first frame portion.

7. The adapter assembly of claim 1, wherein the wall has a first portion extending from the base and a second portion extending from the first portion to the slit, and further wherein a thickness of the wall in a region of the slit is greater than a thickness of the wall along the first portion.

8. The adaptor assembly of claim 1, wherein the slit is centered relative to the base and is linear.

9. The adapter assembly of claim 1, wherein the access port is axially aligned with respiratory port.

10. The adapter assembly of claim 1, wherein the ventilator port intersects the respiratory port of the manifold.

11. The adapter assembly of claim 1, wherein the ventilator port intersects the access port of the manifold.

* * * * *